(12) United States Patent
Azar

(10) Patent No.: US 7,457,434 B2
(45) Date of Patent: Nov. 25, 2008

(54) ADAPTIVELY FOCUSING EXTRA-OCULAR VISION PROSTHESES

(75) Inventor: Dimitri T. Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 559 days.

(21) Appl. No.: 11/098,210

(22) Filed: Apr. 4, 2005

(65) Prior Publication Data
US 2006/0224238 A1    Oct. 5, 2006

(51) Int. Cl.
*G06K 9/00* (2006.01)
(52) U.S. Cl. .................. 382/103; 351/169; 356/124
(58) Field of Classification Search .................. 382/100, 382/103, 106, 107; 351/41, 54, 55, 57, 59, 351/168, 169, 170, 171, 172, 173, 176; 356/3, 356/4.05, 123, 124, 125
See application file for complete search history.

(56) References Cited

U.S. PATENT DOCUMENTS

| 4,181,408 A | * | 1/1980 | Senders | 351/159 |
|---|---|---|---|---|
| 4,190,330 A | | 2/1980 | Berreman | |
| 4,230,942 A | | 10/1980 | Stauffer | |
| 4,309,603 A | | 1/1982 | Stauffer | |
| 4,466,703 A | | 8/1984 | Nishimoto | |
| 4,601,545 A | | 7/1986 | Kern | |
| 4,787,903 A | | 11/1988 | Grendahl | |
| 5,182,585 A | * | 1/1993 | Stoner | 351/41 |
| 5,359,444 A | * | 10/1994 | Piosenka et al. | 349/13 |
| 5,593,437 A | | 1/1997 | Arita et al. | |
| 5,793,704 A | | 8/1998 | Freger | |
| 5,800,530 A | | 9/1998 | Rizzo, III | |
| 6,076,927 A | * | 6/2000 | Owens | 351/118 |
| 6,638,304 B2 | * | 10/2003 | Azar | 623/6.22 |

* cited by examiner

*Primary Examiner*—Anand Bhatnagar
(74) *Attorney, Agent, or Firm*—Fish & Richardson P.C.

(57) ABSTRACT

A vision prosthesis includes an actuator in communication with an extra-ocular lens. The actuator providing a focusing stimulus to vary a focal length of the lens. A rangefinder estimates a range to an object and provides the range estimate to a controller. The controller causes the actuator to generate the focusing stimulus on the basis of the range estimate.

19 Claims, 8 Drawing Sheets

ADAPTIVELY FOCUSING EXTRA-OCULAR VISION PROSTHESES

FIELD OF INVENTION

This invention relates to vision prostheses, and in particular, to extra-ocular vision prostheses.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens, thereby changing its focal length. By selectively deforming the lens in this manner, it becomes possible to focus on objects that are at different distances from the eye. This process of selectively focusing on objects at different distances is referred to as "accommodation."

As a person ages, the lens loses plasticity. As a result, it becomes increasingly difficult to deform the lens sufficiently to focus on objects at different distances. To compensate for this loss of function, it is necessary to provide different optical corrections for focusing on objects at different distances.

One approach to applying different optical corrections is to carry different pairs of glasses and to swap glasses as the need arises. For example, one might carry reading glasses for reading and a separate pair of distance glasses for driving. This is inconvenient both because of the need to carry more than one pair of glasses and because of the need to swap glasses frequently.

Bifocal lenses assist accommodation by integrating two different optical corrections onto the same lens. The lower part of the lens is ground to provide a correction suitable for reading or other close-up work while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

The concept of a bifocal lens, in which different optical corrections are integrated into the same lens, has been generalized to include trifocal lenses, in which three different optical corrections are integrated into the same lens, and continuous gradient lenses in which a continuum of optical corrections are integrated into the same lens. However, just as in the case of bifocal lenses, optical correction for different ranges of distance using these multi-focal lenses relies extensively on relative motion between the pupil and the lens.

SUMMARY

The invention provides a vision prosthesis for restoring a patient's ability to focus on objects at different distances. The vision prosthesis includes a lens whose focal length can automatically be changed, and a rangefinder coupled to that lens for estimating the range to an object that the patient wishes to focus on.

In one embodiment, the variable-focus lens of the vision prosthesis has an index of refraction that varies in response to a focusing stimulus. An actuator in communication with the lens provides the necessary focusing stimulus on the basis of a range estimate from the rangefinder. A controller coupled to the rangefinder and to the actuator causes the actuator to generate a focusing stimulus on the basis of this range estimate.

Because it is the index of refraction that is changed, the vision prosthesis provides control over the focal length of the lens without the need to mechanically move the lens or any portions thereof. The vision prosthesis thus provides a lens of variable focal length with no moving parts and without the complexity and excessive power consumption associated with a moveable system.

In one embodiment of the vision prosthesis, the lens includes a chamber containing a nematic liquid crystal or other material that has a changeable index of refraction. A nematic liquid crystal has an index of refraction that changes in response to an applied electromagnetic field. This change in the index of refraction results in a change in the focal length of the lens.

The actuator for the lens can include a variable voltage source and one or more electrodes coupled to both the variable voltage source and the lens. Alternatively, the actuator can include a variable current source and one or more coils coupled to the variable current source and to the lens. In either case, the actuator generates a field, an electric field in the former case and a magnetic field in the latter case, that can interact with the nematic liquid crystal to selectively alter its index of refraction.

The index of refraction of the lens need not be spatially uniform. By providing a plurality of actuating elements coupled to different local regions of the lens, the index of refraction can be varied at those local regions. This enables the lens to have an effective optical shape that is largely independent of its physical shape. A convex lens can be created, for example, by applying a stronger electric field to the central portion of a planar chamber filled with nematic liquid crystal than to the periphery. This changes the index of refraction at the center more than at the periphery. A lens having a spatially non-uniform index of refraction can be implemented by providing a plurality of electrodes disposed at different portions of the lens. In one aspect of the invention, these electrodes are concentric electrodes. In such a case, the index of refraction can be made a function of distance from the center of the lens.

In an alternative embodiment, the index of refraction can be made a function of more than one spatial variable. For example, the electrodes can be distributed in a two-dimensional grid on the surface of the lens. Such a grid can be a polar grid or a rectilinear grid. Its primary function would be to correct wavefront aberrations present in the eye due to abnormalities in the cornea, the lens, and the ocular media.

In some cases, it may not be possible to vary the index of refraction sufficiently to correct the patient's vision. In such cases, the lens can include one or more lens elements that can be moved so as to bring an image into focus. Such a lens also includes a motor to move the lens elements.

Alternatively, the lens can have a baseline curvature and also be filled with nematic crystal or a material having an index of refraction that can be changed. The baseline curvature can be used to perform a gross correction that can be fine-tuned by locally varying the index of refraction of the lens material.

The rangefinder of the vision prosthesis does not, however, have to rely on the operation of any structure in eye to estimate a distance to an object. For example, the rangefinder can also include an auto-focus system. One example of an auto-focus system includes: an infrared transmitter for illuminating an object with an infrared beam; an infrared receiver for receiving a reflected beam from the object, and a processor coupled to the infrared receiver for estimating a range to the object on the basis of the reflected beam. However, other auto-focus systems can readily be adapted for the use in the vision prosthesis.

To assist the auto-focus system in achieving and maintaining focus, it is often desirable to include a feedback loop coupled to the auto-focus system. One example of a feedback loop includes first and second lenslets posterior to the lens. Each lenslet is in optical communication with an associated photodetector posterior to that lenslet. The distance between the lenslet and its associated photodetector is between the focal lengths of the two lenslets.

Regardless of the type of rangefinder, it is useful to provide an optional manual focusing control for enabling a patient to fine tune focusing of the lens. A manual focusing control enables the patient to correct compensate for minor inaccuracies in the signal provided by the automatic focusing system. With a manual focusing control, the rangefinder can in fact be dispensed with. Thus, in yet another embodiment of the invention, the apparatus includes a manual focusing control instead of a rangefinder.

These and other features and advantages of the invention will be apparent from the following detailed description and the accompanying figures, in which:

DETAILED DESCRIPTION

Figure 1:
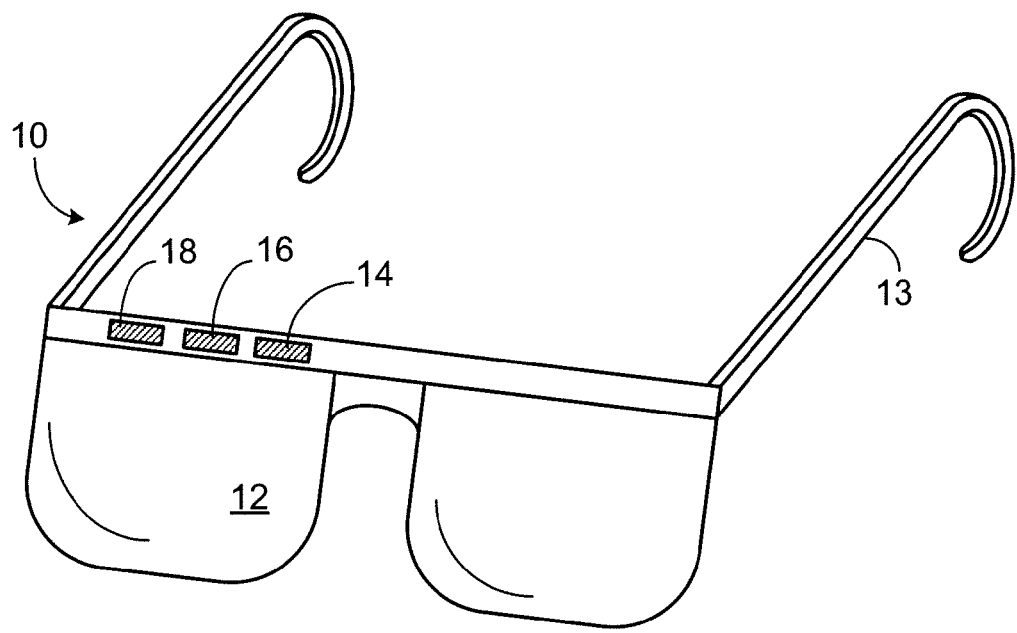
FIG. 1 shows an extra-ocular vision prosthesis mounted on an eyeglass frame.
Figure 2:
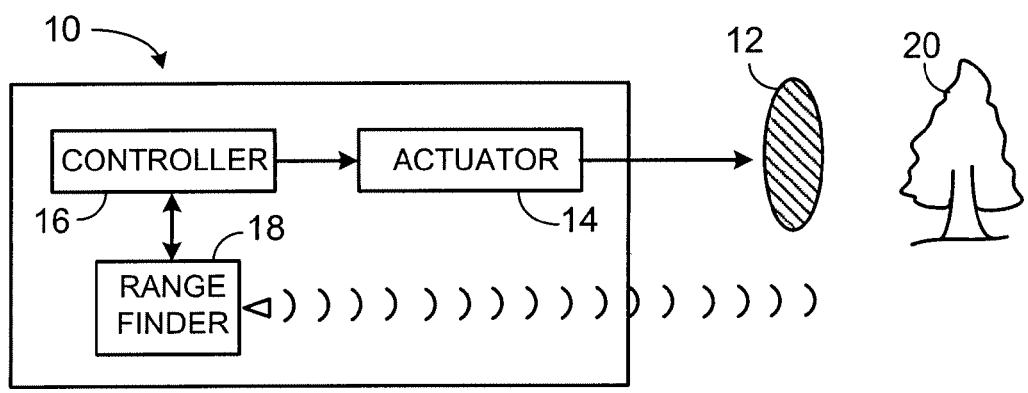
FIG. 2 is a block diagram of the extra-ocular vision prosthesis shown in FIG. 1.

Referring to FIG. 1, an extra-ocular vision prosthesis 10 for adaptively focusing a lens 12, is mounted on a frame 13 and worn in the manner of conventional eyeglasses. The lens 12 is one whose index of refraction can be made to vary in response to a focusing signal provided to an actuator 14 by a controller 16, as shown in FIG. 2. The nature of the focusing signal provided to the actuator 14 controls the extent to which the index of refraction is changed. The controller 16 in turn generates its control signal on the basis of a distance signal provided by the rangefinder 18.

The controller 16 is typically a microcontroller having instructions encoded therein. These instructions can be implemented as software or firmware. However, the instructions can also be encoded directly in hardware in, for example, an application-specific integrated circuit. The instructions provided to the microcontroller include instructions for receiving, from a rangefinder 18, data indicative of the distance to an object-of-regard 20, and instructions for processing that data to obtain a focusing signal. The focusing signal alters the lens' index of refraction to focus an image of the object-of-regard 20 on the retina.

A power source (not shown) supplies power to the controller 16, the range finder 18, and the actuator 14. A single power source can provide power to all three components. However, the vision prosthesis 10 can also include a separate power source for any combination of those components that require power. A suitable power source is a rechargeable battery.

Lenses and Actuators

The lens 12 is any combination of one or more refracting elements having an overall focal length responsive to the actuator 14.

In some embodiments, the lens 12 directs light through a nematic liquid-crystal whose index of refraction varies in response to an applied electric field. In that case, the actuator 14 includes one or more electrodes in electrical communication with the lens 12.

Figure 3:
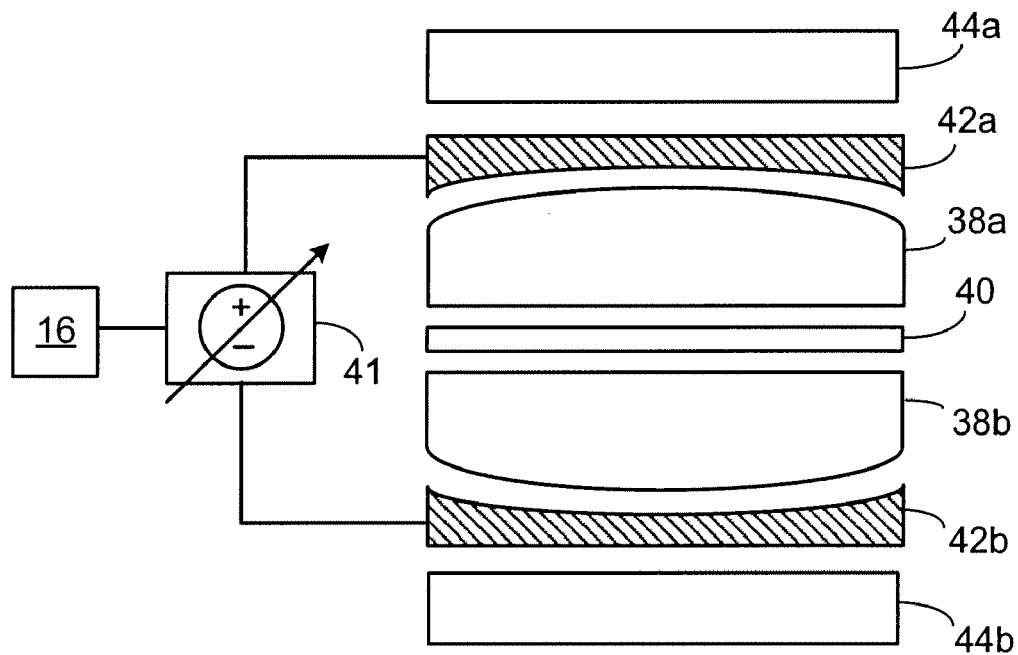
FIGS. 3-5 show two embodiments of the lens and actuator of the visual prosthesis shown in FIG. 2.

In one embodiment of the lens 12, shown in exploded view in FIG. 3, first and second curved chambers 38a, 38b filled with nematic liquid-crystal are separated by a transparent plate 40. In this embodiment, the actuator 14 includes a variable voltage source 41 connected to two transparent electrodes 42a, 42b disposed on an outer surface of each curved chamber 38a, 38b. The variable voltage source 41 generates a variable voltage in response to instructions from the controller 16. First and second transparent outer layers 44a, 44b cover the first and second electrodes 42a, 42b respectively.

When the variable voltage source 41 applies a voltage, the first and second electrodes 42a, 42b impose an electric field in the nematic liquid-crystal. This electric field tends to reorient the directors of the nematic liquid-crystal, thereby changing its index of refraction. A lens assembly of this type is described fully in U.S. Pat. No. 4,190,330, the contents of which are herein incorporated by reference.

Figure 4:
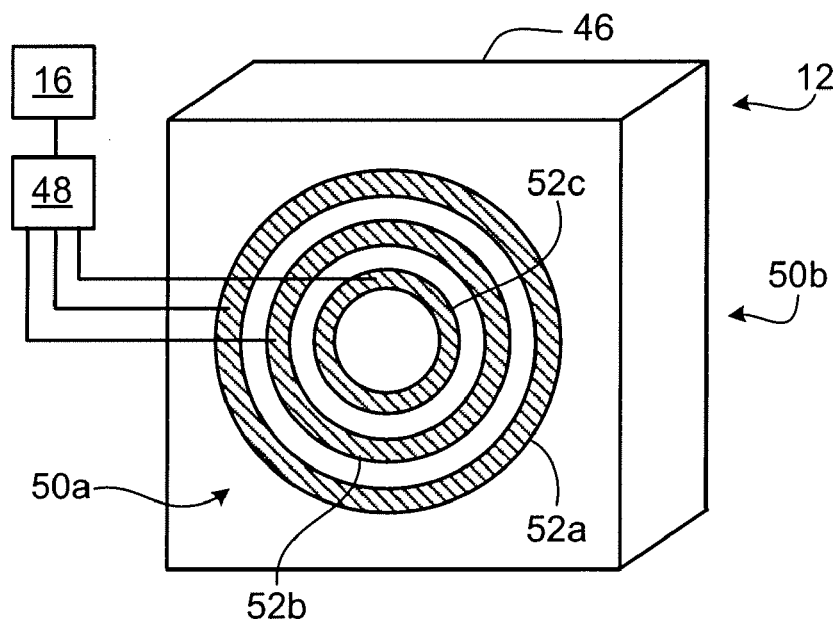

In another embodiment, shown in FIG. 4, the lens 12 includes a thin chamber 46 filled with nematic liquid-crystal. In this case, the actuator 14 includes a variable voltage source 48 and first and second sets 50a, 50b of electrodes 52a-c disposed on opposed planar surfaces of the thin chamber 46. Each of the electrodes 52a-c is individually addressable by the controller 16. A voltage maintained across an electrode 52a from the first set 50a and a corresponding electrode from the second set 50b results in an electric field across a local zone of the nematic liquid-crystal adjacent to those electrodes. This electric field reorients the directors, and hence alters the index of refraction, within that zone. As a result, the index of refraction can be made to vary at different points of the lens 12.

Figure 5:
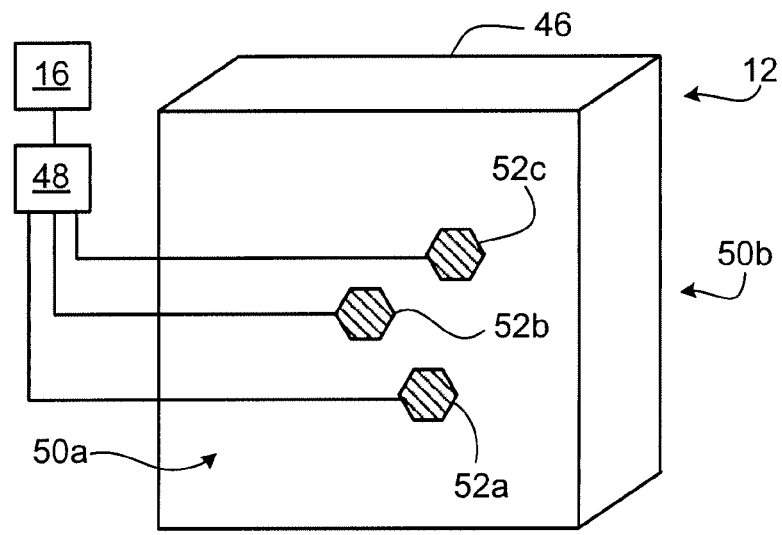

FIG. 4 shows a lens assembly having concentric electrodes 52a-c. A lens assembly of this type is described fully in U.S. Pat. No. 4,466,703, the contents of which are herein incorporated by reference. In this embodiment, the index of refraction can be altered as a function of distance from the center of the lens 12. However, individually addressable electrodes 52a-c can also be arranged in a two-dimensional array on the surface of the lens 12. When this is the case, the index of refraction can be varied as a function of two spatial variables. The grid of electrodes 52a-c can be a polar grid, as shown in FIG. 4, or a rectilinear grid, as shown in FIG. 5. The electrodes 52a-c can be distributed uniformly on the grid, or they can be distributed more sparsely in certain regions of the lens 12 and more densely in other regions of the lens 12.

The extent to which the index of refraction of a nematic liquid crystal can be changed is limited. Once all the directors in the nematic liquid crystal have been polarized, increasing the magnitude of the imposed electric field has no further effect. A nematic liquid crystal in this state is said to be saturated. To change the focal length beyond the point at which the nematic crystal is saturated, a lens 12 can also include one or more lens elements that are moved relative to each other by micromechanical motors (not shown).

Alternatively, the lens 12 can have a baseline curvature and also be filled with nematic crystal. The baseline curvature can be used to perform a gross correction that can be fine-tuned by locally varying the index of refraction of the lens material.

In another embodiment, the lens 12 is made up of a multiplicity of lenslets, as shown in FIG. 5, each of which has its own baseline curvature and each of which is filled with nematic crystal. An individually addressable electrode is then connected to each of the lenslets. In this embodiment, both the lens curvature and the index of refraction can be varied locally as a function of two spatial variables.

However, in other embodiments, the lens 12 can also direct light through a material whose index of refraction varies in response to an applied magnetic field. In this case, the actuator 14 is a magnetic field source, such as a current-carrying coil, in magnetic communication with the lens 12.

In yet other embodiments, the lens 12 is one that is similar to a zoom lens in a camera. Such a lens 12 includes one or more refracting elements that move in relation to each other. In such cases, the actuator 14 is a small electric motor that causes movement of the lens elements.

Other embodiments include lenses 12 that have, as a refracting element, a deformable fluid filled lens bag, with the amount of fluid in the lens bag controlling the shape of the bag, and hence the focusing properties of the lens bag. In these embodiments, fluid can be moved into or our of the lens bag using artificial muscle actuators of the type described in copending U.S. application Ser. No. 10/895,504, filed on Jul. 21, 2004, the contents of which are herein incorporated by reference. Alternatively, such artificial muscle actuators can be configured to deform or move a lens.

Figure 6:
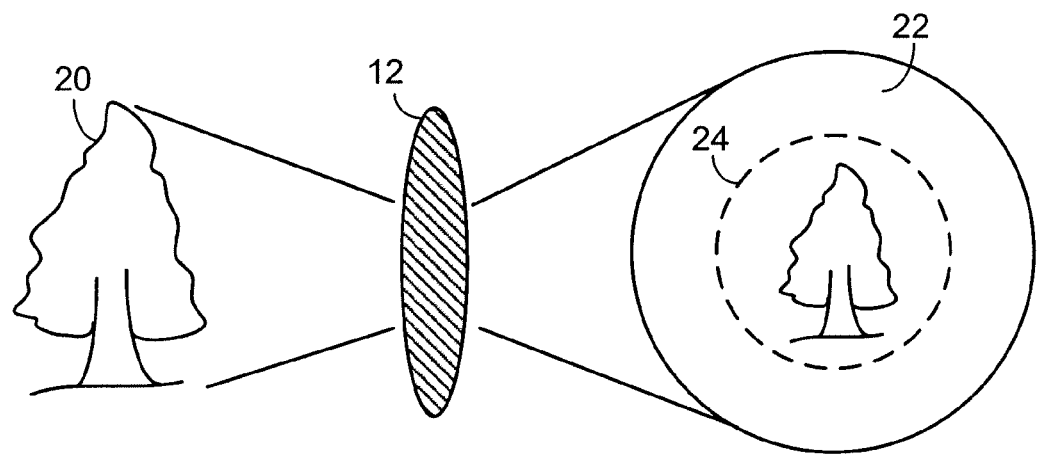
FIG. 6 illustrates the field-of-view and the target region of a lens
Figure 7:
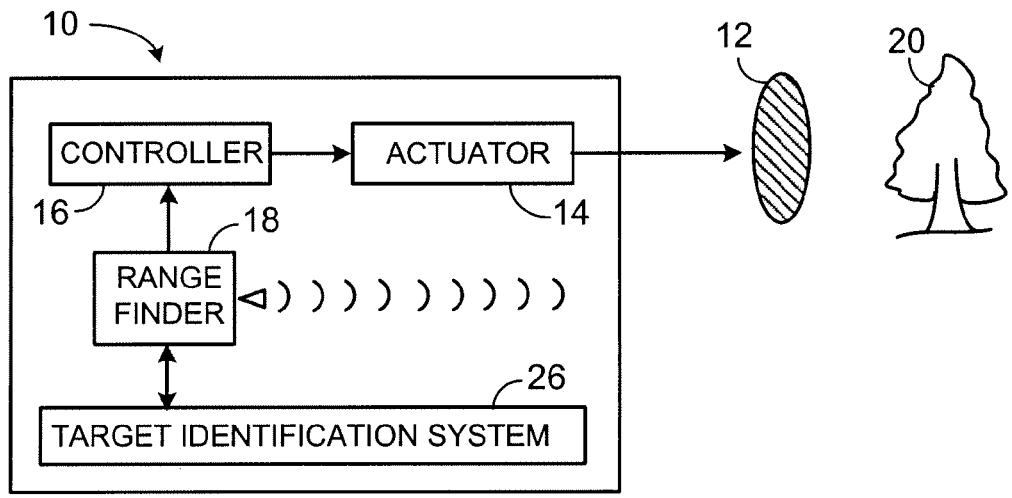
FIG. 7 is a block diagram of an extra-ocular vision prosthesis with a target identification system.

Referring to FIG. 6, the lens 12 defines a field-of-view 22 that encompasses images of various objects, one of which is an image of the object-of-regard 20 upon which a wearer wishes to focus. The correct focusing of the lens 12 thus includes two steps. The first step is that of identifying, within the field-of-view 22, a target region 24 upon which to focus. This target region 24, when correctly identified, encompasses the image of the object-of-regard 20. Having identified the target region 24, the next step is to identify a range to the object-of-regard 20 within that target region 24. The second function is carried out by the rangefinder 18. The first function is carried out by an optional target identification system 26, in communication with the rangefinder 18, as shown in FIG. 7.

Another actuator/lens combination can include a transparent magnet as described in Gich, et al., "High-coercivity ultralight Transparent Magnets," Applied Physics Letters, vol. 82 (24), pp. 4307-4309 Jun. 16, 2003, the contents of which are incorporated herein by reference. In such magnets, iron needles in an aerogel hare an orientation that responds to a magnetic field. These needles affect the optical properties of the aerogel. As a result, one can apply a magnetic field to control the optical properties of a lens that incorporates an aerogel.

To the extent that the orientation of the needles responds differently to light of different polarization, a lens incorporating a transparent magnet can be used to adaptively control the polarization state of light entering the eye.

Transparent magnets of this type can also be used in an intraocular lens. In such a case, the frame can include a magnetic field source which can then be used to adaptively control the orientation of the iron needles within the intraocular lens. Such control can include control over the refractive properties of the intra-ocular lens or control over the polarization-transmitting properties of the intra-ocular lens.

Rangefinders

One example of a rangefinder 18 is that used in auto-focus cameras. Such a rangefinder transmits a beam of radiation, detects a reflected beam, and estimates a distance to an object on the basis of that reflected beam.

The output of the rangefinder 18 can then be communicated directly to the controller 16. In this case, the target region is assumed to be a pre-selected region, such as a central spot, in the field of view. A rangefinder 18 of this type is thus an "attitude-dependent" rangefinder because it determines a distance to an object-of-regard 19 solely on the basis of the attitude, or orientation, of the frame 13 on which it is mounted.

Attitude-dependent rangefinders can use any form of radiation, with convenient examples including electromagnetic radiation and acoustic radiation. In the case of electromagnetic radiation, infrared wavelengths are suitable because of the propagation characteristics of such radiation and the ready availability of appropriate transmitters and receivers. In the case of acoustic radiation, the same can be said for ultrasonic radiation.

Figure 8:
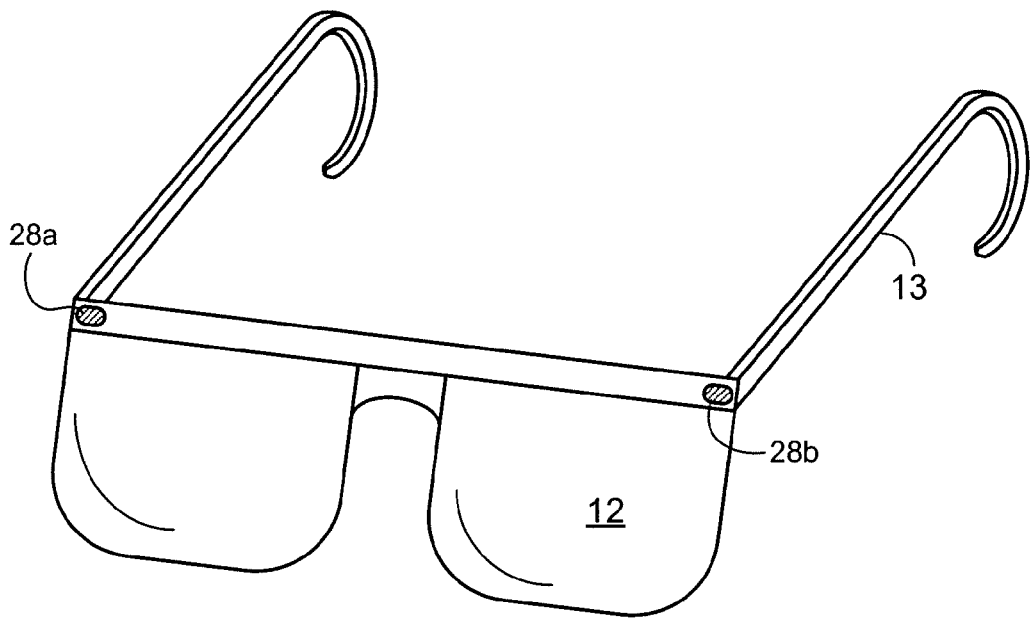
FIG. 8 shows an eyeglass frame on which are mounted a pair of sensors used in connection with creating a topographic map of the field-of-view.
Figure 9:
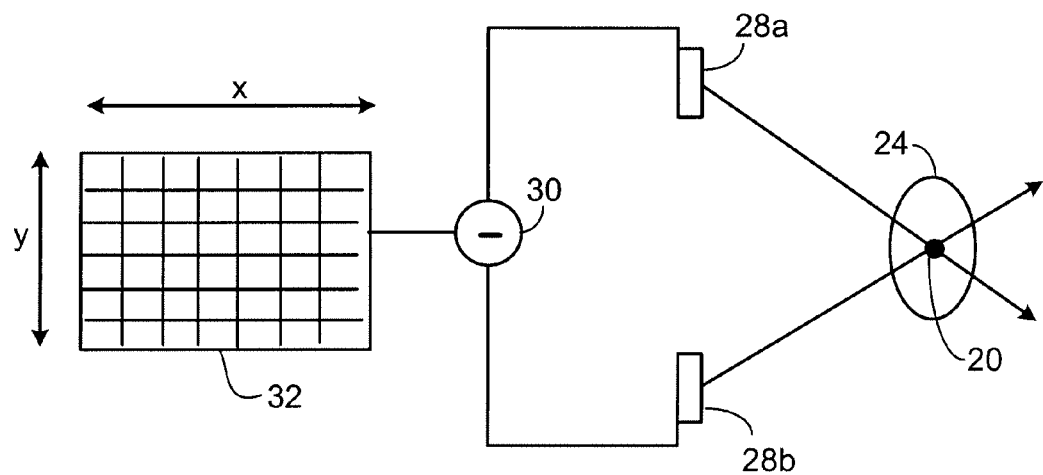
FIG. 9 is a block diagram of a rangefinder that receives signals from the sensors in FIG. 8.
Figure 10:
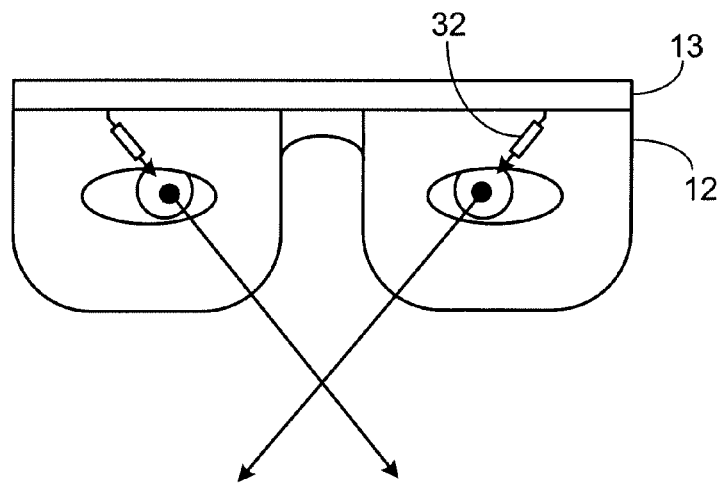
FIG. 10 shows a visual prosthesis that includes an eye-tracker.

Another example of an attitude-dependent rangefinder 18, shown in FIG. 8, exploits the parallax difference between two measurements obtained from sensors 28a, 28b or receivers that are displaced relative to each other. For a particular region 24 in the field-of-view 22, the parallax-dependent rangefinder 18 estimates a distance to an object in that region 24 on the basis of a parallax difference associated with that region.

One example of a parallax-dependent rangefinder 18 features lenses 28a, 28b mounted on either side of the frame 13. To maximize parallax differences between them, these lenses 28a, 28b are mounted as far from each other as possible. Each lens 28a forms an image on a CCD (charged-coupled device) in much the same way that a lens forms an image in a digital camera.

Image signals representative of the two images thus formed are provided to a 20 differencing element 30, which creates a two-dimensional topographic map 32 showing the differences between the two image signals. The extent of the differences between the two image signals varies across the topographic map 32, with the greatest differences located at those portions of the topographic map 32 that correspond to nearby objects. The term "topographic" map 32 is an apt one in this case because objects at infinity can be regarded as being at a virtual "sea level" and objects nearby can be viewed as being on virtual "mountains" extending toward the wearer from this virtual "sea level."

The topographic map 32 is periodically updated as the wearer's field of view changes. This allows the topographic map 32 to remain accurate if the wearer turns his head, or if an object enters or leaves the wearer's field of view.

Another type of rangefinder 18 includes a biofeedback system that estimates an actual distance to an object. One such system includes a pair of eye-trackers 32 that observe medial convergence. It is well known that when one focuses on a nearby object, the pupils move medially, whereas when one focuses on a distant object, the pupils point straight ahead. Thus, after suitable calibration, a rangefinder 18 that detects and quantifies medial convergence can infer the distance to an object-of-regard 20.

Another type of rangefinder 18 is a biofeedback system that relies on the synkinetic reflex to infer a wearer's attempt to focus at a particular distance. Such a system includes an eye-tracker 32 to observe pupil size, and/or inter-pupillary distance, and a photo sensor to measure ambient lighting. Biofeedback systems of this type generally require a calibration step in which a wearer's pupillary responses and/or inter-pupillary separations in attempted accommodations under various lighting conditions are recorded and graphed.

Additional accuracy may be achieved by providing a way for the wearer to zero the system, for example by pushing a button while accommodating at infinity. This calibration avoids errors arising from variations in pupil size associated with states of increased or decreased sympathetic and/or parasympathetic release as well states of increased or decreased esotropia or exotropia when the wearer is fatigued.

It is also known that when a person intends to focus on a nearby object, the iris 26 expands, thereby contracting the pupil 60. Thus, another embodiment of a biofeedback system features an eye-tracker 32 to measure this contraction and to provide therefrom information indicative of the distance to the object-of-regard.

Target Identification Systems

Figure 11:
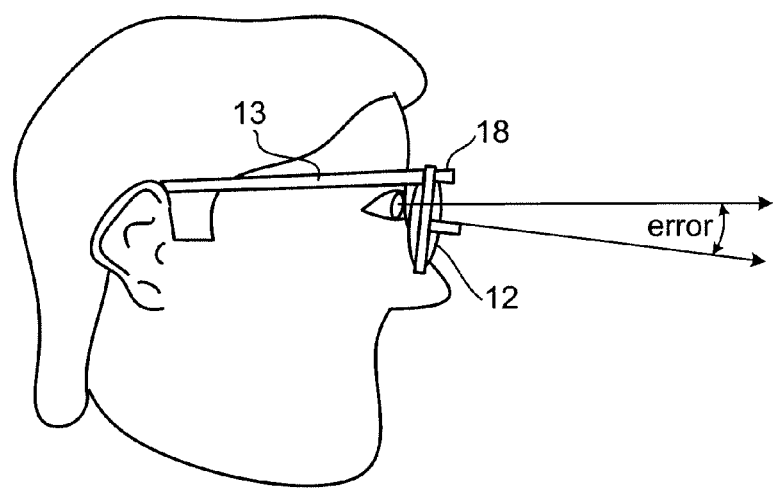
FIG. 11 illustrates the cause of a focusing error that may occur in connection with an attitude-dependent rangefinder.

A drawback of both attitude-dependent rangefinders and of parallax-dependent rangefinders is that they are prone to error resulting from an inconsistency between the attitude of the frame and the direction of a person's gaze, as illustrated in FIG. 11. For example, if one were gazing straight ahead, but one's eyeglass frame 13, perhaps due to perspiration, insisted on sliding down one's nose, then a vector normal to the lens 12 would point downward even though the object of regard might be straight ahead. In this case, the rangefinder 18 would mistakenly conclude that the target region 24 was lower in the field-of-view 22. Alternatively, a vector normal to the lens 12 may point straight ahead, even as the wearer discreetly glances out of the corner of his eye. If one were to rely solely on the attitude of the frame 13 to determine a distance to an object, both these scenarios would result in an error in identifying the target region 24, and hence, a focusing error.

One approach to alleviating this difficulty is to make the lenses 12 small enough so that any error between the direction of the wearer's gaze through the glasses and the attitude of the frames is reduced below some threshold. Essentially, this has the effect of making the field-of-view 24 smaller, thereby making it more difficult to incorrectly identify the target region 24. A wearer of such eyeglasses would thus encounter disappointment when glancing out the corner of his eye since no optical correction would be available in such a case.

Other approaches to alleviating this difficulty involve providing a target identification 26 into the visual prosthesis 10, as shown in FIG. 7.

Figure 12:
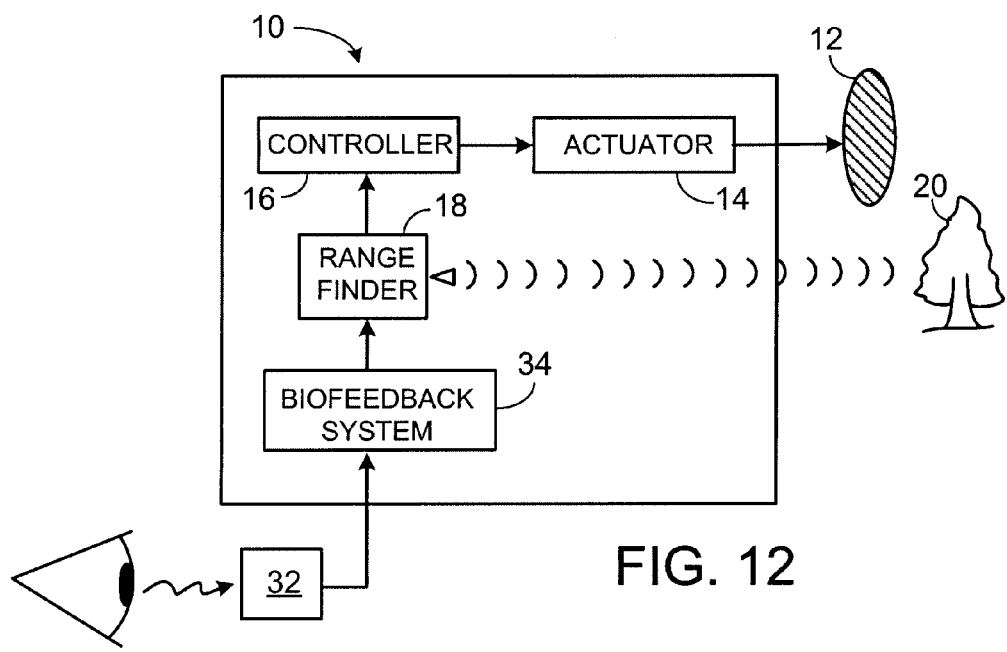
FIG. 12 is a block diagram of a vision prosthesis with a biofeedback system for identifying a target area.

One example of a target identification system 26 is a goniometric biofeedback system 34, as shown in FIG. 12. Exemplary goniometric biofeedback systems 34 include an eye-tracker 32 that attempts to determine the direction in which the eyes are oriented. Such eye-trackers 32 include those that rely on simplified iris, limbus, and/or pupil detectors from which one can infer the direction of the wearer's gaze. Eye-trackers 32 can also rely on Purkinje images to infer the direction of gaze, with the separation and relative orientation of the Purkinje images providing information indicative of the direction of gaze.

Eye-trackers 32 can also infer the direction of gaze from the apparent shape of the pupil. For example, depending on the eye-tracker's point of view, the pupil might appear circular when the direction of gaze is straight ahead and appear progressively more oval as the gaze direction moves toward the peripheral field. The eccentricity of the oval and the direction of the oval's major axis would provide cues for determining the gaze direction.

Another embodiment of the goniometric biofeedback system 34 infers the direction of gaze from the positions of magnets that have been implanted in a moving portion of the eye as described in copending U.S. application Ser. No. 10/847,515 filed on May 17, 2004, the contents of which are herein incorporated by reference. In this embodiment, the locations of the magnets are tracked by one or more inductive coils, or proximity sensors, mounted in the eyeglass frame.

Goniometric biofeedback systems 34 that determine a direction of gaze cooperate with the rangefinder to provide a more accurate estimate of the distance to an object of regard than either could provide separately. For example, a goniometric biofeedback system 34 could estimate the direction of a person's gaze and provide that information to an attitude-dependent rangefinder 18. The rangefinder 18 could then cause an infra-red transceiver to point in the direction estimated by the eye-tracker 32. The pointing of the infra-red transceiver can be achieved by driving a small motor that swivels the infra-red transmitter in a direction consistent with the eye-tracker's estimate of the gaze direction.

A goniometric biofeedback system 34 can also cooperate with a parallax-dependent rangefinder. For example, suppose the eye-tracker 32 determines that the wearer's gaze is directed along a ray extending along a particular angle. A simple geometric transformation can then determine the intersection of that ray with the topographic map 32. That intersection point has, associated with it, a distance determined on the basis of the parallax difference between the two images. This parallax-derived distance is then provided to the controller 16, which causes the actuator 14 to focus the lens 12 for optimal viewing of an object located at that distance from the wearer.

Additional embodiments of the rangefinder 18 include feedback mechanisms to enhance the vision prosthesis' ability to achieve and maintain focus on an object-of-regard 20.

Figure 13:
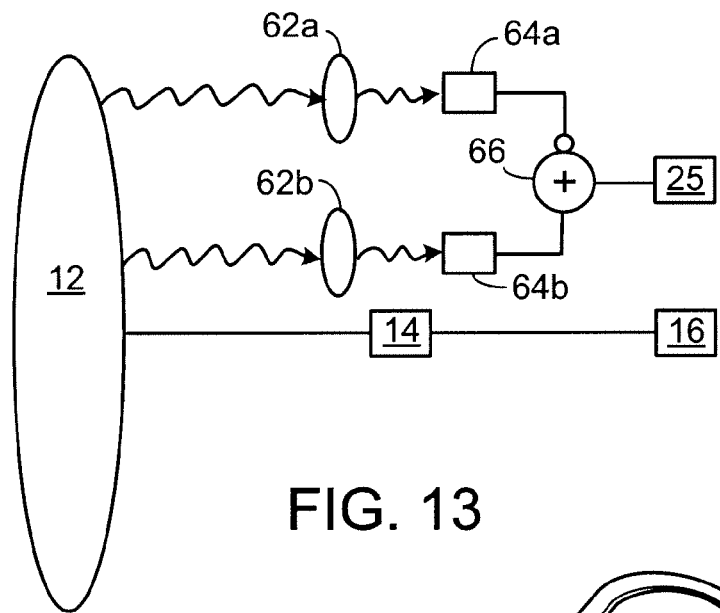
FIG. 13 is a diagram of a feedback loop for maintaining focus on an object of regard.

In a feedback mechanism as shown in FIG. 13, first and second lenslets 62a, 62b are disposed posterior to the intraocular lens 12. The first and second lenslets 62a, 62b are preferably disposed near the periphery of the lens 12 to avoid interfering with the wearer's vision. A first photodetector 64a is disposed at a selected distance posterior to the first lenslet 62a, and a second photodetector 64b is disposed at the same selected distance posterior to the second lenslet 62b. The focal length of the first lenslet 62a is slightly greater than the selected distance, whereas the focal length of the second lenslet 62b is slightly less than the selected distance.

The outputs of the first and second photodetectors 64a, 64b are connected to a differencing element 66 that evaluates the difference between their output. When the output of the differencing element 66 is zero, the lens 12 is in focus. When the output of the differencing element 66 is non-zero, the sign of the output identifies whether the focal length of the lens 12 needs to be increased or decreased, and the magnitude of the output determines the extent to which the focal length of the lens 12 needs to change to bring the image into focus. A feedback mechanism of this type is disclosed in U.S. Pat. No. 4,309,603, the contents of which are herein incorporated by reference.

In any of the above embodiments of the rangefinder 18, a manual control can also be provided to enable a wearer to fine-tune the focusing signal. The rangefinder 18 can then use any correction provided by the wearer to calibrate its range estimates so that the next time that that range estimate is made, there will be no need for fine-tuning by the wearer. This results in a self-calibrating vision prosthesis 10.

Power Supplies

Figure 14:
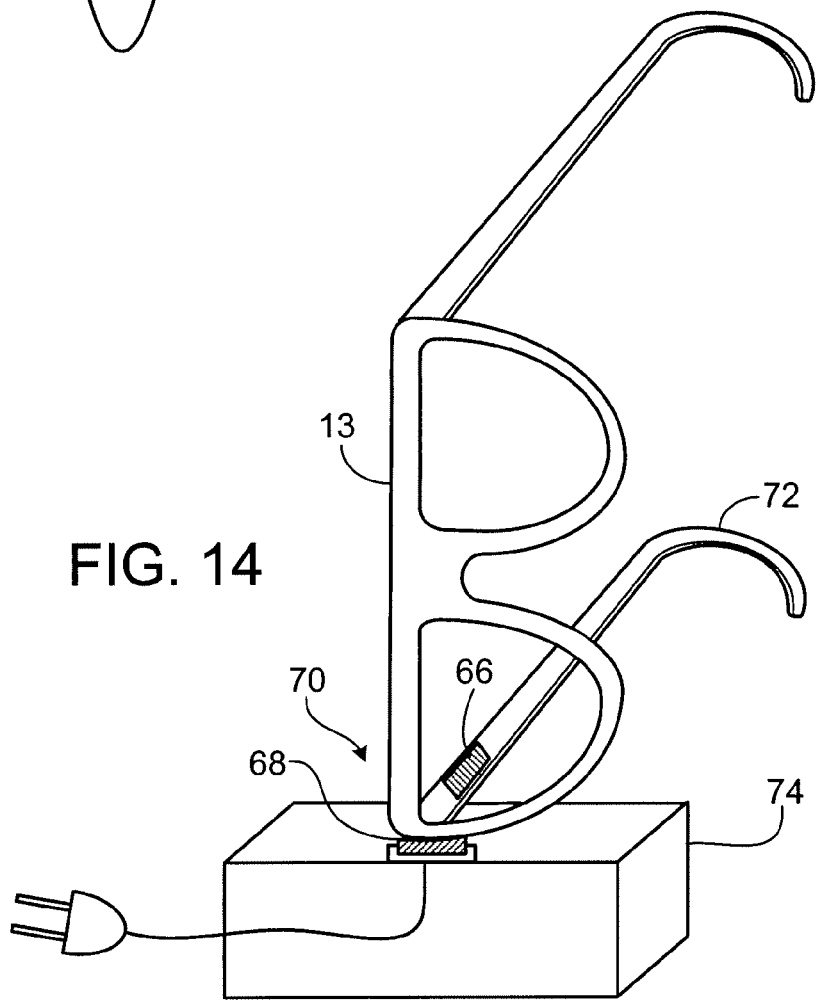
FIG. 14 shows a frame in a position that permits a power supply to be recharged.

A suitable power supply for the vision prosthesis is a rechargeable battery 66 mounted discretely in the frame 13, as shown in FIG. 14. Electrical contacts integrated into a hinge mechanism 70 function as a switch 68 to disconnect the battery 66. When the glasses are not being worn, the temples 72 are generally folded, thereby opening the switch 68. When the glasses are being worn, the temples 72 are generally unfolded, thereby closing the switch 68. The integration of the switch 68 with the hinge 72. Thus provides a way to conserve power when the vision prosthesis 10 is not in use.

The contacts on the switch 68 are likewise configured to mate, when the temple 72 is folded, with corresponding contacts on a dock 74 that provides power for recharging the battery 66.

Figure 15:
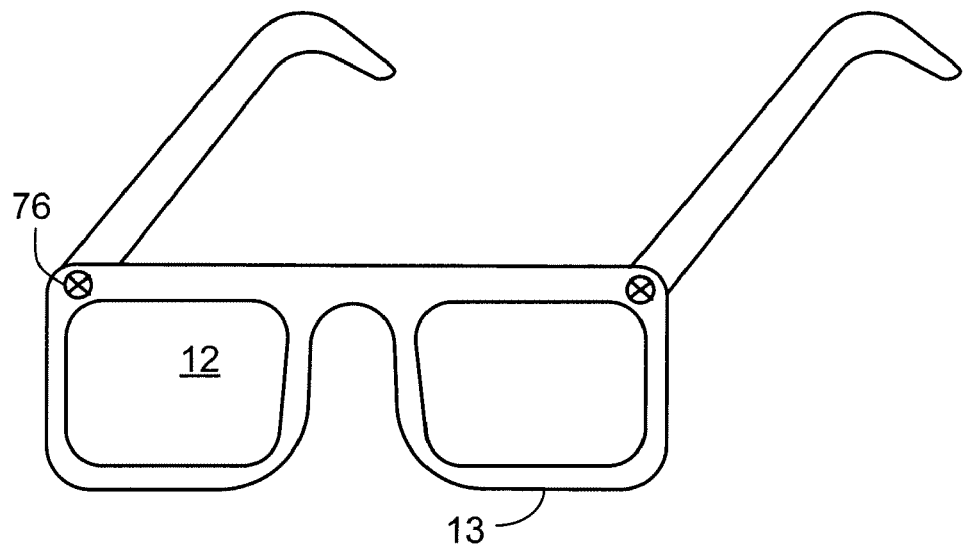
FIGS. 15 and 16 show frames having photo-voltaic power supplies.
Figure 16:
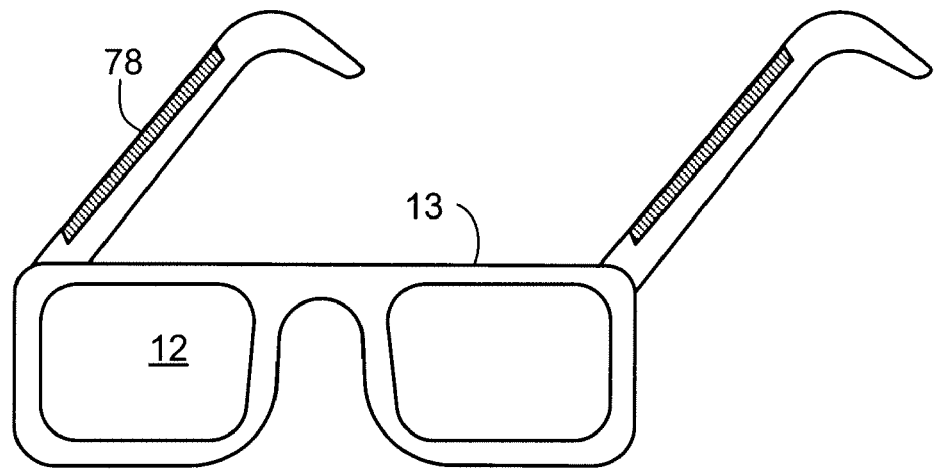

The vision prosthesis 10 can also be powered by a photovoltaic cell 76 mounted on the frame 13 as shown in FIG. 15 or an array 78 of photovoltaic cells 78 mounted on the temples 72, as shown in FIG. 16. An advantage of the configuration shows in FIG. 16 is that considerable power can be generated without requiring the wearer to face a bright light.

The power source can also be a hybrid power source, with photovoltaic cells 76 providing power in daylight and the battery 66 providing power in dim light. In such a hybrid system, excess power from the photovoltaic cells 76 can be shunted to the battery 66, thereby permitting the battery to recharge under bright ambient lighting.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what I claim as new and secured by letters patent is:

The invention claimed is:

1. A vision prosthesis comprising:
   an actuator in communication with an extra-ocular lens, the actuator providing a focusing stimulus to vary a focal length of the lens;
   a biofeedback system for identifying, at least in part on the basis of cues provided by a wearer of the vision prosthesis, a gaze direction leading to an object;
   a rangefinder for estimating a range to the object; and
   a controller in communication with the rangefinder and the actuator, the controller being configured to cause the actuator to generate the focusing stimulus on the basis of the range estimate.

2. The vision prosthesis of claim 1, wherein the biofeedback system is configured to detect a feature of the wearer's eye, and to estimate the gaze direction at least in part on the basis of the feature.

3. The vision prosthesis of claim 1, wherein the rangefinder comprises:
   a radiation source oriented to illuminate the object; and
   a radiation detector for detecting a reflection from the object.

4. The vision prosthesis of claim 1, wherein the range finder comprises:
   a first sensor for forming a first image of the object;
   a second sensor for forming a second image of the object; and
   a differencing element for generating difference data indicative of a difference between the first and second images.

5. Eyeglasses comprising:
   a frame;
   a variable-focus lens mounted on the frame; and
   a vision prosthesis as recited in claim 1.

6. A method for assisting a patient in focusing on an object, the method comprising:
   providing an extraocular lens for the patient to look through, the extraocular lens having a variable focal length;
   identifying, at least in part on the basis of cues provided by a wearer of the vision prosthesis, a gaze direction leading to an object within a field of view of the extraocular lens;
   estimating a distance to the object; and
   causing the focal length to change in response to the estimate.

7. The method of claim 6, wherein estimating a distance to an object comprises:
   detecting a feature of an eye, the feature being selected to depend on a gaze direction of the eye;
   estimating, at least in part on the basis of the feature, a gaze direction; and
   selecting the object to be along the gaze direction.

8. The method of claim 7, wherein detecting a feature comprises detecting locations of magnets implanted into the eye.

9. The method of claim 7, wherein detecting a feature comprises detecting an apparent shape of a pupil.

10. The method of claim 7, wherein detecting a feature comprises detecting Purkinje images.

11. The method of claim 7, further comprising calibrating the feature with a known gaze direction.

12. The method of claim 6, wherein estimating a distance comprises detecting a feature of an eye, the feature being selected to depend on an attempted accommodation of the eye.

13. The method of claim 12, wherein detecting a feature comprises detecting an inter-pupillary distance.

14. The method of claim 12, wherein detecting a feature comprises detecting a diameter of a pupil.

15. An apparatus for correcting vision, the apparatus comprising:
   means for identifying, on the basis of cues provided by a wearer of an extraocular lens, a gaze direction leading to an object in the field of view of the extraocular lens;
   means for estimating a range to the object; and
   means for varying a focal length of an extra-ocular lens on the basis of the range estimate.

16. The apparatus of claim 15, wherein the means for estimating a range comprises means for estimating a range on the basis of a feature of at least one eye.

17. The apparatus of claim 16, further comprising means for identifying a direction leading to the object.

18. The apparatus of claim 17, wherein the means for estimating a range is configured to estimate a range to an object lying in the direction identified by the means for identifying a direction.

19. A vision prosthesis comprising:
an actuator in communication with an extra-ocular lens, the actuator providing a focusing stimulus to vary a focal length of the lens;
a biofeedback system for estimating the distance to an object in the field of view of the extra-ocular lens on the basis of cues provided by a wearer of the vision prosthesis; and
a controller in communication with the rangefinder and the actuator, the controller being configured to cause the actuator to generate the focusing stimulus on the basis of the range estimate.

* * * * *